US00PP29368P2

(12) United States Plant Patent
Thompson

(10) Patent No.: US PP29,368 P2
(45) Date of Patent: Jun. 12, 2018

(54) RASPBERRY PLANT NAMED 'PBBRASP1348'

(50) Latin Name: ***Rubus idaeus* L.**
Varietal Denomination: PBBrasp1348

(71) Applicant: Pacific Berry Breeding, LLC, Salinas, CA (US)

(72) Inventor: Ellen Thompson, Watsonville, CA (US)

(73) Assignee: Pacific Berry Breeding, Salinas, CA (US)

( * ) Notice: Subject to any disclaimer, the term of this patent is extended or adjusted under 35 U.S.C. 154(b) by 0 days. days.

(21) Appl. No.: 15/731,007

(22) Filed: Apr. 5, 2017

(51) Int. Cl.
*A01H 5/08* (2018.01)

(52) U.S. Cl.
USPC ..... Plt./204

(58) Field of Classification Search
USPC ..... Plt./204
See application file for complete search history.

*Primary Examiner* — Annette H Para
(74) *Attorney, Agent, or Firm* — King IP Law; Joshua King

(57) ABSTRACT

The present application relates to new and distinct cultivar of primocane-fruiting raspberry named 'PBBrasp1348'. The new variety reliably provides balanced heavy crop load on both primocanes and floricanes, with large, glossy, non-darkening, broad-conic fruits of medium adherence to the receptacle. Plants possess high vigor, produce high numbers of spawn, and branch naturally along the main cane. Susceptibility to yellow rust (*Phragmidium rubi-idaei*) has been observed. Field tolerance to Raspberry Bushy Dwarf Virus (RBDV) and *Phytophthora* root rot has been observed.

5 Drawing Sheets

Latin name of the genus and species of the plant claimed: *Rubus idaeus* L.

Variety denomination: 'PBBrasp1348'.

BACKGROUND AND SUMMARY

The new primocane-fruiting raspberry cultivar designated as 'PBBrasp1348' is described herein. Botanically known as *Rubus idaeus* L., this new variety resulted from a hand-pollinated cross of female parent 'Pacific Gema' (U.S. Plant Pat. No. 28,080), a release from the same program, and the unpatented male parent 'E10-22'. Hand-pollination occurred in April 2012 and seeds from this controlled cross were subsequently harvested, cleaned, germinated, and established as seedlings in spring 2013 in Watsonville, Calif., Santa Cruz County, USA.

'PBBrasp1348' was first identified in a substrate block, where seedlings had individually been planted into 3 liter pots, in September 2013 in Watsonville, Calif. This selection was first propagated asexually by crown division (of the original potted mother-plant) in autumn 2013 in Watsonville, Calif. The crown on the original plant was parted into basal cane pieces (approximately 15 cm long) with root attached and planted into soil, in a selection plot elsewhere on the farm, resulting in a 10-fold increase in plant material. Harvest and postharvest data were collected from this larger plot of 'PBBrasp1348' for two years, from 2014 through 2016.

In January 2014, additional root pieces from the original mother-plant were planted into an on-site greenhouse. Two actively growing etiolated shoots were forced from roots, transplanted and potted. Once established, these shoots were sent to Lafayette, Oreg., USA, where vegetative material was explanted and established in vitro for micropropagation. Subsequent asexual propagation was done on-site in Watsonville, Calif. and, along with tissue-cultured plantlets, 'PBBrasp1348' was evaluated extensively over the next several years for performance and genetic stability.

The present cultivar, 'PBBrasp1348' offers many advantages over the existing, patent-pending cultivar and maternal parent, 'Pacific Gema' (U.S. Plant Pat. No. 28,080). Average fruit size of 'PBBrasp1348' is larger, berries detach more easily from the receptacle, are of lighter color, and are more broadly-conic in shape (versus the narrow conic shape of 'Pacific Gema'). Yield of 'PBBrasp1348' is also greater than 'Pacific Gema', on average, possibly due to its heavy branching habit. The lighter color, high gloss, ease of fruit detachment and improved yield offers significant advantages to growers, who require fast picking speeds and non-darkening color, combined with glossiness which helps to extend shelf life of the fruit (by appearing to stay fresher for a longer period of time). The larger, broadly-conic berries help growers fill baskets more quickly, leading to increased harvest efficiency. Root vigor, subsequent cane vigor, and floricane budbreak for 'PBBrasp1348' is similar to 'Pacific Gema'.

In contrast to the unpatented male parent 'E10-22', the present cultivar 'PBBrasp1348' is significantly greater in vigor, plant fitness and offers larger fruit. In particular, the amount of suckers that 'PBBrasp1348' produces is two-fold of its paternal parent. This improvement is of significant importance to growers, who rely upon the regenerative ability of suckers, in order to guarantee subsequent crops. The desirable light color of 'PBBrasp1348' is similar to that of the male parent. In contrast to the darker fruit color and lower yields of previous cultivar releases from the same program, including 'Pacific Deluxe' (U.S. Plant Pat. No. 21,074) and 'Pacific Royale' (U.S. Plant Pat. No. 21,536), 'PBBrasp1348' offers a significant improvement for commercial raspberry growers. Thus, these characteristics help define 'PBBrasp1348' as a new and distinct cultivar of primocane-fruiting raspberry. 'PBBrasp1348' may be recognized by its high vigor, strong suckering habit, uniform floricane budbreak, heavily-branched canes, large broadly-conic berries of light color and high gloss, and which consistently yield more than existing varieties within the same program.

BRIEF DESCRIPTION OF THE PHOTOGRAPHS

DETAILED DESCRIPTION

Figure 1:
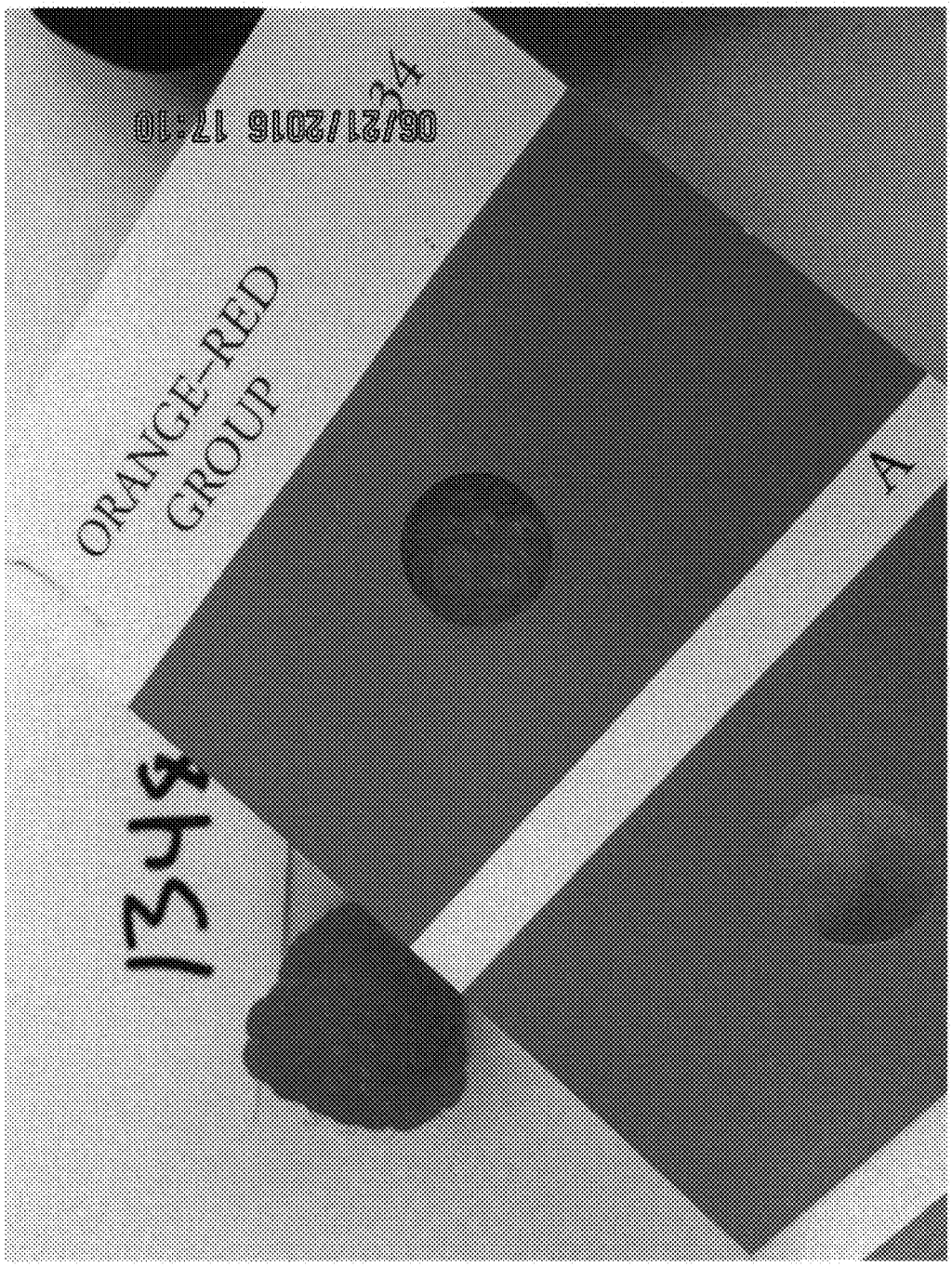
FIG. 1 is a photograph showing the fresh fruit color of raspberry cultivar 'PBBrasp1348'.
Figure 2:
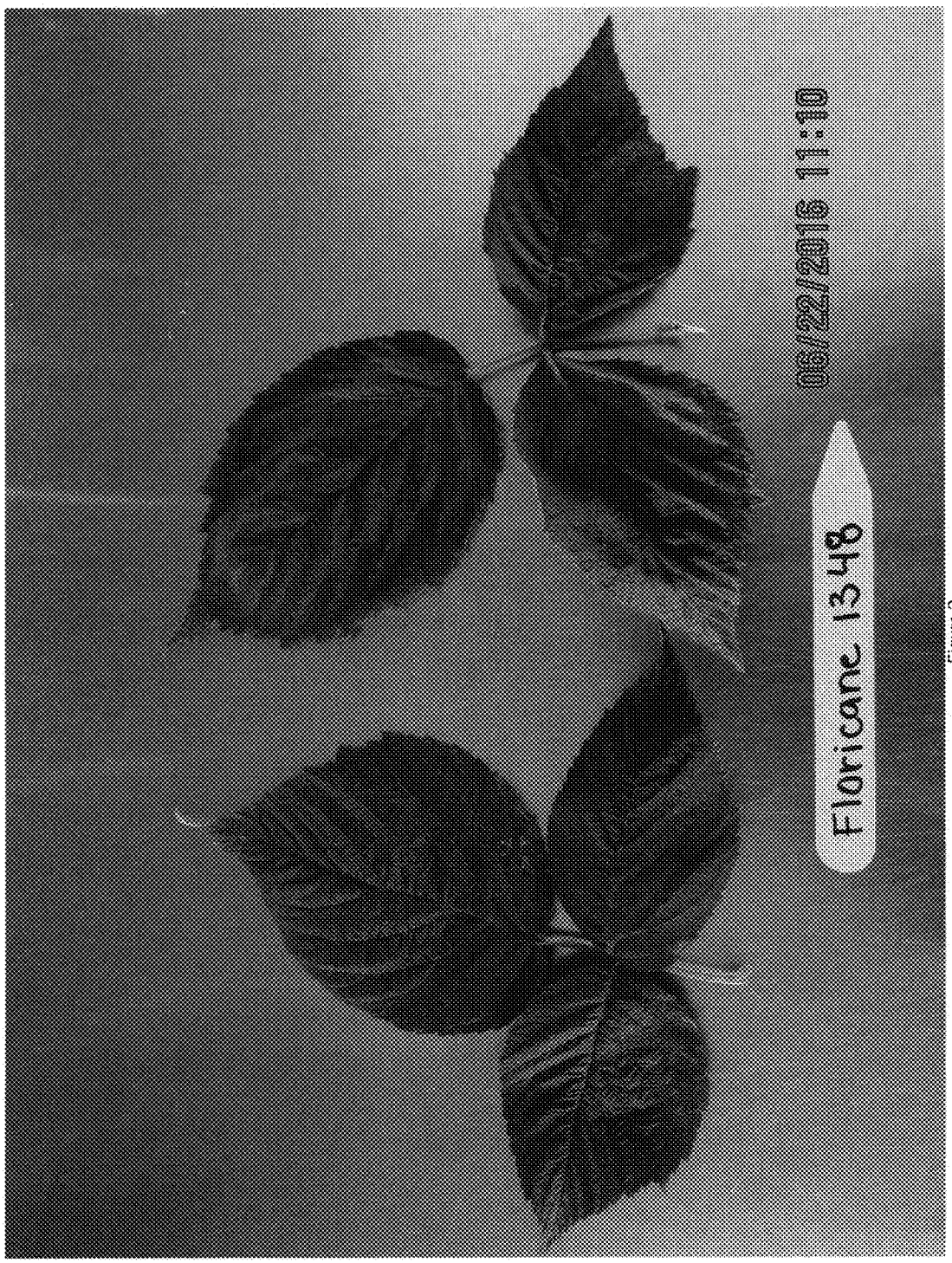
FIG. 2 is a photograph displaying leaf size and morphology of raspberry cultivar 'PBBrasp1348'.
Figure 3:
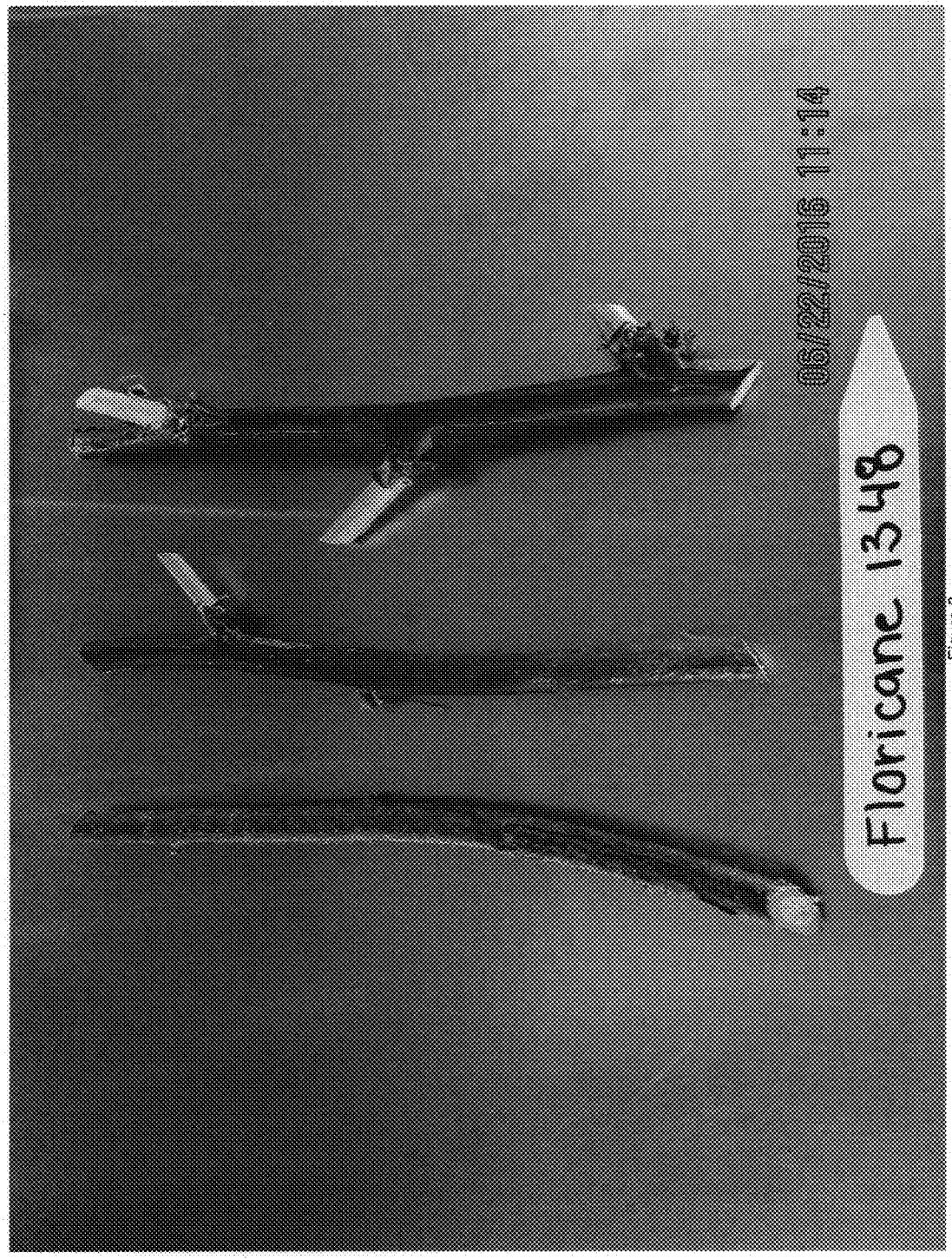
FIG. 3 is a photograph showing the floricane and spine color of raspberry cultivar 'PBBrasp1348'.
Figure 4:
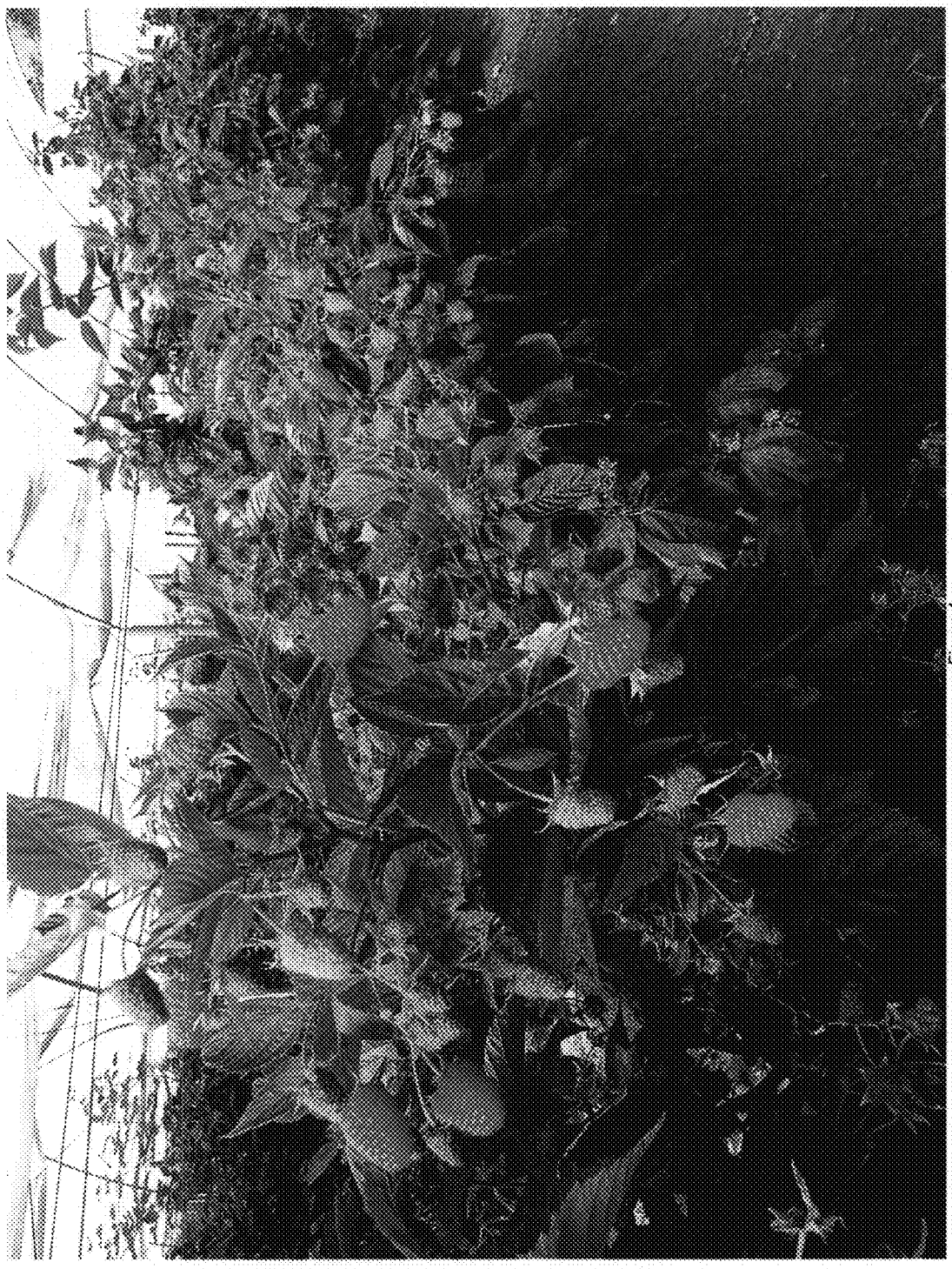
FIG. 4 is a photograph displaying the canopy, primocane crop load and architectural habit of raspberry cultivar 'PBBrasp1348'.
Figure 5:
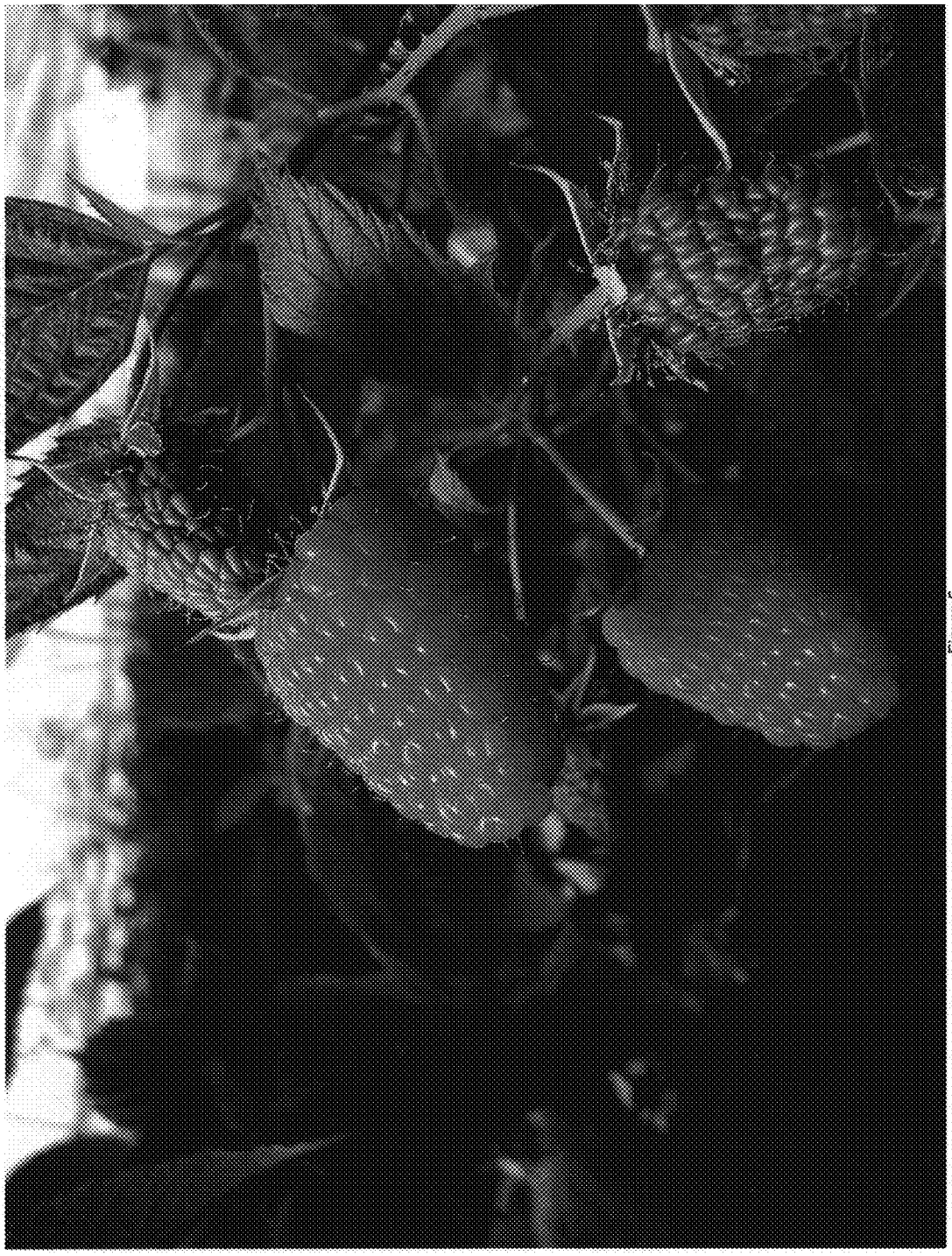
FIG. 5 is a photograph showing the drupelet development, fruit size and color on primocanes of cultivar 'PBBrasp1348'.

Note: statements of characteristics herein represent exemplary observations of the cultivar herein and will vary depending on time of year, location, annual weather, etc.

Cultivar name: 'PBBrasp1348'.

Classification:

*Family*.—Rosaceae.

*Botanical name*.—*Rubus idaeus* L.

*Common name*.—Raspberry.

Parentage:

*Female parent*.—'Pacific Gema' (U.S. Plant Pat. No. 28,080).

*Male parent*.—'E10-22'. As noted above, compared to the maternal parent, 'Pacific Gema', the average fruit size of 'PBBrasp1348' is larger, berries detach more easily from the receptacle, are of lighter color, and are more broadly-conic in shape (versus the narrow conic shape of 'Pacific Gema'). Yield of 'PBBrasp1348' is also greater than 'Pacific Gema', on average, possibly due to its heavy branching habit. The lighter color, high gloss, ease of fruit detachment and improved yield offers significant advantages to growers, who require fast picking speeds and non-darkening color, combined with glossiness which helps to extend shelf life of the fruit (by appearing to stay fresher for a longer period of time). The larger, broadly-conic berries help growers fill baskets more quickly, leading to increased harvest efficiency. Root vigor, subsequent cane vigor, and floricane budbreak for 'PBBrasp1348' is similar to 'Pacific Gema'. Compared to the unpatented male parent 'E10-22', the present cultivar 'PBBrasp1348' is significantly greater in vigor, plant fitness and offers larger fruit. In particular, the amount of suckers that 'PBBrasp1348' produces is two-fold of its paternal parent. This improvement is of significant importance to growers, who rely upon the regenerative ability of suckers, in order to guarantee subsequent crops. The desirable light color of 'PBBrasp1348' is similar to that of the male parent.

Growing location for the observations herein: Watsonville, Calif., USA.

Time of year (season): Early summer for floricanes, and late summer for primocanes.

Age of plants used for this discussion: Crown age of about 3 years and a cane age of about 8 months.

Age of plants used for the photographs in the Figures: Crown age of about 3 years and a cane age of about 4-8 months.

Type of greenhouse covering or growing structure, or field: High tunnel over field-grown plants.

Light: Natural. Color terminology refers to The R.H.S. Colour Chart, Royal Horticultural Society, Fifth Edition, London, United Kingdom (2007). Observations for floricanes herein were made in June 2016. Observations for primocanes herein were made in August 2016.

Plant:

*Form/shape*.—Vase.

*Growth habit*.—Erect.

*Height*.—1.4 m as measured from cane base to apex.

*Spread*.—0.5 m as measured from terminal leaflet tip to terminal leaflet tip.

*Propagation methods*.—Division.

*Time to initiate and develop roots*.—21 days.

*Root description*.—Fibrous. Generally of medium diameter with a smooth, glossy texture.

Primocanes:

*Cane diameter*.—Base — 1.1 cm|Middle — 0.9 cm|Tip — 0.4 cm.

*Cane length*.—1.4 m.

*Number of node per cane*.—40. Internode length: Base — 7.9 cm|Middle — 8.2 cm|Tip — 8.1 cm.

*Number of canes/hill*.—8.

*Cane color*.—RHS 144A.

*Spines*.—Present. Spine density: Base — 10/cm$^2$|Middle — 2/cm$^2$|Tip — 2/cm$^2$. Spine shape: Acuminate. Spine length: 0.16 cm. Spine width: 0.10 cm. Spine apex descriptor: Acuminate. Spine color: RHS 178A.

*Vegetative bud shape*.—Rounded.

*Vegetative bud length*.—2.0 cm.

*Vegetative bud diameter* (*base*).—0.9 cm.

*Vegetative bud diameter* (*tip*).—0.08 cm.

*Vegetative bud color*.—RHS 143C.

Floricanes:

*Cane diameter*.—Base — 1.2 cm|Middle — 0.9 cm|Tip — 0.8 cm.

*Cane length*.—94.9 cm.

*Number of nodes per cane*.—15. Internode Length: Base — 10.5 cm|Middle — 6.2 cm|Tip — 8.2 cm.

*Cane color*.—Lower Cane — RHS 175C|Upper Cane — RHS 175A.

*Spines*.—Present. Spine density: Base — 3/cm$^2$|Middle — 4/cm$^2$|Tip — 4/cm$^2$. Spine shape: Acuminate. Spine length: 0.2 cm. Spine width: 0.02 cm. Spine apex descriptor: Acuminate. Spine color: RHS 165A.

*Reproductive bud shape*.—Truncate.

*Reproductive bud length*.—1.4 cm.

*Reproductive bud diameter* (*base*).—0.8 cm.

*Reproductive bud diameter* (*tip*).—0.05 cm.

*Reproductive bud color*.—RHS 143C.

*Reproductive bud texture*.—Pubescent.

*Winter hardiness*.—Unknown outside of USDA Hardiness Zone 9b (Watsonville, Calif.). This cultivar is best adapted to the mild coastal conditions of California.

*Drought/heat tolerance*.—Pollen viability and fruit quality of raspberry generally begins to decline above 30° C. This is consistent with observations of 'PBBrasp1348'. Raspberries are generally not drought tolerant, and 'PBBrasp1348' has not been tested in unirrigated plots.

Leaves:

*Complete leaf*.—Length: 23.6 cm. Width: 20.9 cm. Number of leaflets: 3 to 5.

*Terminal leaflet*.—Size. Length: 12.9 cm. Width: 9.6 cm. Length/Width ratio: 1.4. Leaf shape of apex: Acuminate. Leaf shape of base: Cordate. Leaf margin: Serrate. Leaf texture: Rigid interveinal puckering. Number of serrations per leaf: 101 serrations. Leaf shape of serrations: Flexuous-Flexuous. Leaf color: Upper Surface: RHS N137A. Lower Surface: RHS N138C. Leaf venation pattern: Palmate. Leaf venation color: Upper surface: RHS N137A. Lower surface: RHS N144C. Leaf pubescence density: Present on underside only; moderate. Color of leaf pubescence: RHS N138C. Shape of leaf in cross-section: Oval. Number of leaflets/leaf: Primocane: 3-5 Floricane: 3. Interveinal blistering within leaf: Present. Leaf glossiness: Matte.

*Primocane leaves*.—Petiole length: 12.7 cm. Petiole diameter: 0.3 cm. Petiole Color: Upper: RHS 144C. Lower: RHS 144C. Rachis length: 5.6 cm. Stipule length: 2.4 cm. Stipules per leaf: 2. Stipule Width: 0.004 cm. Stipule Color: Upper Surface: RHS 144B. Lower Surface: RHS 144B.

*Terminal leaflet*.—Length: 14.0 cm. Width: 10.4 cm. Rachis length: 4.7 cm.

*Distal lateral leaflet*.—Length: 9.9 cm. Width: 5.7 cm. Petiolule length: Sessile.

*Basal lateral leaflet*.—Length: 11.7 cm. Width: 8.2 cm. Petiolule length: 0.6 cm.

*Floricane leaves*.—Petiole length: 5.3 cm. Stipule length: 0.6 cm. Stipules per leaf: 2. Stipule Width: 0.006 cm. Stipule Color: Color Upper surface: RHS 144B. Lower surface: RHS 144B.

*Terminal leaflet*.—Length: 12.9 cm. Width: 9.6 cm. Rachis length: 2.3 cm. Distal lateral leaflet: Not Present. Length: N/A. Width: N/A.

*Petiolule*.—Length: N/A. Diameter: N/A. Color: N/A.

*Basal lateral leaflet*.—Length: 9.5 cm. Width: 6.2 cm.

*Petiolule*.—Length: 0.4 cm. Diameter: 0.1 cm. Color: Upper: RHS 144A. Lower: RHS 144B.

Flowers:

*Time of flowering* (50% *of plants at first flower*).—Approximately 110 days after planting (on primocanes).

*Flower size*.—Length: 1.1 cm. Diameter: 1.0 cm.

*Fragrance*.—None.

*Peduncle*.—Length: 3.8 cm. Diameter: 0.2 cm. Color: RHS 143C. Pubescence: Present, very sparse. Texture: Smooth, with spines.

*Perianth*.—Flowering trusses shape: Truncate.

*Petals*.—Color: Upper — RHS 157C|Lower — RHS 157D. Number per flower: 5 petals. Shape: Obovate. Length: 0.9 cm. Width: 0.4 cm. Apex description: Rounded. Base Descriptor: Cuneate. Margin descriptor: Entire. Texture: Smooth with visible striations.

*Sepals*.—Quantity: 5 sepals. Length: 1.3 cm. Width: Base — 0.6 cm|Mid — 0.4 cm|Tip — 0.06 cm. Color: RHS 143C. Apex descriptor: Acuminate. Margin descriptor: Entire. Texture: Pubescent.

*Pedicel*.—Color: RHS 143C. Length: 3.2 cm. Diameter: 0.1 cm.

Reproductive organs:

*Self-fertile*.—Yes.

Male:

*Stamen number*.—117.

*Filament*.—Length: 0.5 cm. Diameter: 0.03 cm. Color: RHS 155A.

*Anther*.—Length: 0.007 cm. Diameter: 0.003 cm. Color: RHS 199D.

*Pollen*.—Color: RHS 199D. Amount: Moderate.

Female:

*Style*.—Length: 0.04 cm. Diameter: 0.01 cm. Color: RHS 157A.

*Stigma*.—Length: 0.03 cm. Diameter: 0.01 cm. Color: RHS 158D.

*Ovary*.—Length: 0.01 cm. Diameter: 0.07 cm. Color: N144D.

Fruit:

*Predominant shape*.—Broad Conical.

*Weight* (*g*).—5.5 g.

*Length*.—2.7 cm.

*Width*.—Base — 1.9 cm|Mid — 1.8 cm|Tip — 1.5 cm.

*Length/width ratio*.—1.7 cm.

*Receptacle*.—Length: 1.3 cm. Diameter: Base — 0.5 cm|Mid — 0.3 cm|Tip — 0.2 cm. Color: RHS 160B.

*Drupelet*.—Length: 0.5 cm. Diameter: 0.3 cm. Number: 90. Weight: 0.04 g.

*Fruit color*.—External: RHS 34A. Internal: RHS 182A.

*Firmness of skin*.—Moderate.

*Firmness of flesh*.—Moderate.

*Hollow center*.—Present.

*Number of fruit per node*.—9.

*Time of ripening* (50% *of plants with first fruit*).—150 days after planting, on average.

*Time of fruiting*.—Spring to summer on floricanes; late summer and early autumn on primocanes.

*Type of bearing*.—Remontant.

*Fruit yield*.—15,972 lb/a, on average.

*Average brix*.—8.8.

*Typical market use*.—Fresh.

*Keeping quality*.—Excellent.

*Shipping quality*.—Good.

Pest and disease resistance: 'PBBrasp1348' shows susceptibility to yellow rust (*Phragmidium rubi-idaei*), a common fungal disease under commercial conditions. 'PBBrasp1348' has exhibited field tolerance to Raspberry Bushy Dwarf Virus (RBDV) and *Phytophthora* root rot.

What is claimed is:

1. A new and distinct cultivar of Raspberry plant named 'PBBrasp1348' as described and shown herein.

* * * * *